United States Patent [19]

Hochstein

[11] 4,007,629
[45] Feb. 15, 1977

[54] METHOD AND APPARATUS FOR MONITORING OIL DEGRADATION

[76] Inventor: Peter A. Hochstein, 14020 15 Mile Road, Sterling Heights, Mich. 48077

[22] Filed: Nov. 4, 1975

[21] Appl. No.: 628,810

[52] U.S. Cl. .................................. 73/53; 73/64; 235/92 MT

[51] Int. Cl.² ...................................... G01N 33/30

[58] Field of Search ......... 73/53, 64, 117.3, 339 R, 73/344, 363; 235/92 MT

[56] References Cited

UNITED STATES PATENTS

| | | | |
|---|---|---|---|
| 2,814,201 | 11/1957 | Cotton | 73/339 R |
| 3,275,808 | 9/1966 | Knudsen | 235/92 MT |

*Primary Examiner*—Richard C. Queisser
*Assistant Examiner*—Joseph W. Roskos
*Attorney, Agent, or Firm*—McGlynn and Milton

[57] ABSTRACT

A method and apparatus for monitoring the degradation of oil, particularly crankcase oil. A first sensor includes creep material positioned under constant stress in thermal contact with the oil to act as an analogue computer as it changes its length in response to temperature and the time at that temperature to register the degradation of oil due to the oil's oxidation. In addition, a second sensor registers the contamination of the oil by adding the number of times the oil is heated but not heated to a high enough predetermined temperature to disperse the water, acids and sludge which contaminate the oil. When the combination of these outputs reach a predetermined limit, a signal is provided.

49 Claims, 9 Drawing Figures

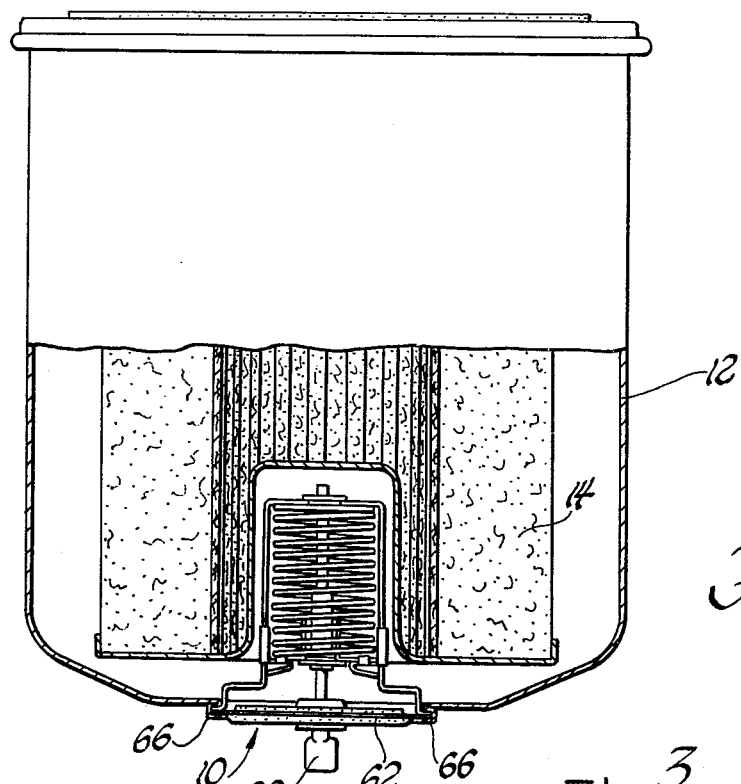
Fig. 1
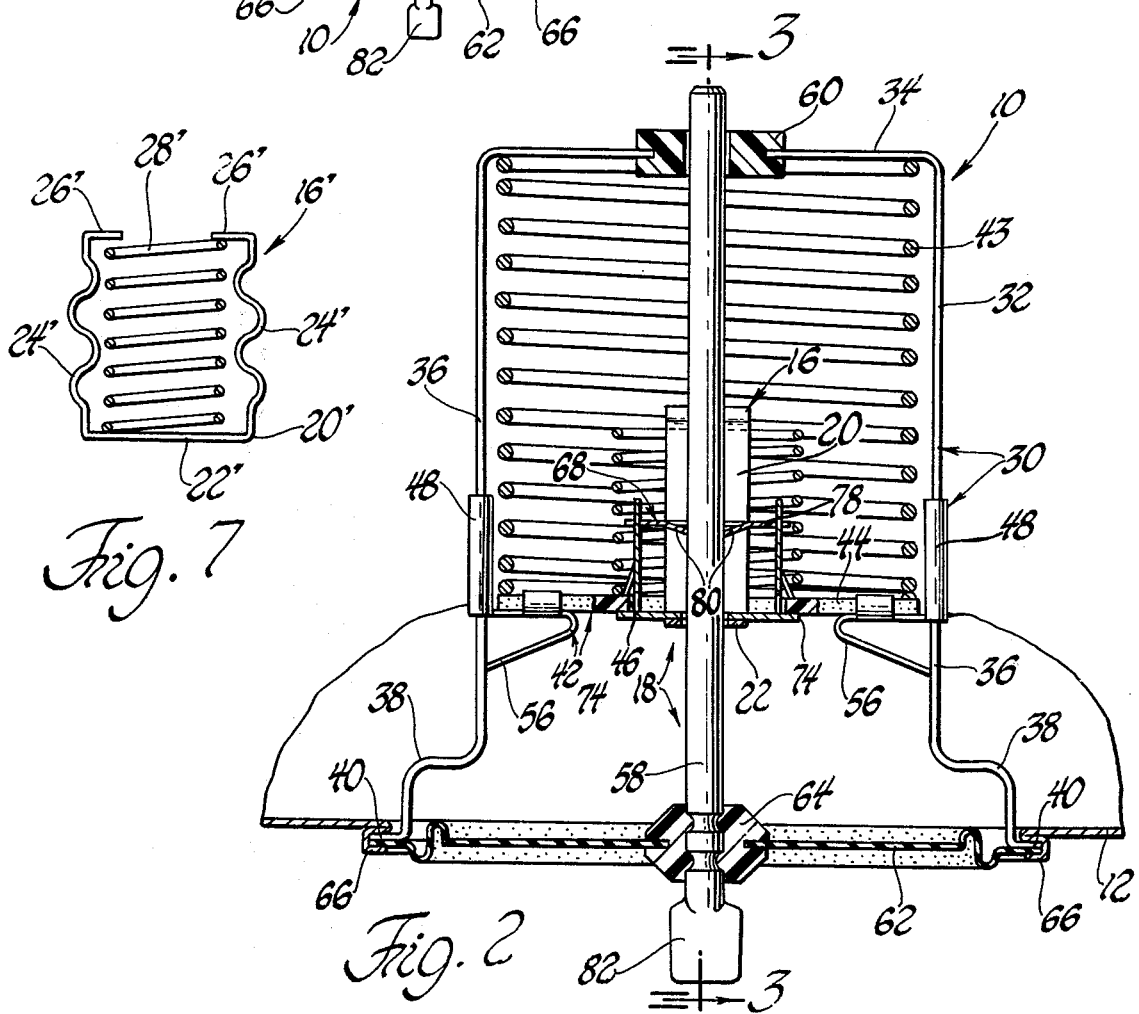
Fig. 7
Fig. 2

METHOD AND APPARATUS FOR MONITORING OIL DEGRADATION

This invention relates to the monitoring of the degradation of oil and is particularly adaptable for monitoring the degradation of lubricating oil such as that utilized in the internal combustion engine of an automotive vehicle, although as will become more clear hereinafter, the invention is suitable for monitoring the change in a material undergoing a thermally activated process which follows an exponential curve, the operand of the exponent being the base of the natural system of logarithms.

Although the invention has broader application, it was particularly developed to solve a problem associated with the lubricating oil used in the internal combustion engines of automotive vehicles. As is well known, the manufacturer of an automobile suggests to the automotive owner the intervals at which the oil should be changed. Normally, this will be after so many miles or after so long a time period. These suggested periods are based upon figures which would include most average drivers, however, there are a significant number of automotive users who will not fall within the parameters suggested by the automotive manufacturer. For example, a user may drive a station wagon automobile towing a 22 foot trailer with a boat for 16 hours and only cover 800 miles yet the engine temperature was sufficiently high that the oil will have degraded to the point that it should be changed at the end of that 16 hours. Continued use of that engine without changing the oil could ruin the engine long before the mileage suggested by the manufacturer for changing the oil is reached. At the other end of the spectrum a driver may continuously drive his automobile under conditions whereby the oil is not even close to the degradation requiring that it be changed when the automobile reaches the number of miles at which the manufacturer suggests the oil be changed. As will be appreciated, there are significant warranty problems to the manufacturer associated with changing the oil, particularly with large truck engines which are continuously operated and/or operated under severe conditions such as a heavily loaded truck travelling across the desert. Additionally, millions of gallons of oil are wasted because engine oil is changed when the oil remains very acceptable.

There are devices known to the prior art which provide a signal indicating that the oil should be changed. Most of them provide a signal indicating that the oil should be changed after a given number of engine hours, a given number of engine revolutions alone or in combination with the operating temperature. These devices, however, do not actually monitor the degradation of the oil itself and are only slightly better than changing the oil at established mileage or time intervals. More sophisticated systems are known but they are expensive electronic systems which only approximate the degradation of the motor oil. Such devices are only practical with large expensive trucks where the cost can be justified because it is offset in the prevention of expensive repairs.

There is nothing known which monitors the degradation of engine lubricating oil by direct contact with the oil and which is responsive to the two components of the total oil degradation.

The first component in the degradation of the lubricating oil is the oxidation of the oil which is an exponential function of the oil temperature and time at the temperature. The oxidation of the oil, of course, affects the oil's viscosity and the viscosity of the oil, in turn, affects engine wear. The oxidation of the oil and, consequently, the viscosity of the oil increases exponentially with time, as discussed in more detail by R. H. Kabel in his Society of Automotive Engineering paper, S.A.E. Trans. 79 (3) 1888 (1970). The oxidation of the oil increases the solid particles in the oil which, in turn, affects engine wear. It has been shown that an engine run under specific test conditions yields an oil with nominally 20 percent weight solid particles and a hundred fold increase in the viscosity. The solid particles resulting from the oxidation were no larger than 5 to 8 microns in diameter and were dispersed in an oil phase which was nominally 34 percent oxidized. These solid particles would not, of course, be filtered out by conventional oil filters. Additionally, the acid numbers of 11 and 64 were measured for the oil and solid particles respectively. The high acidity of the solid particles is, of course, detrimental to the engine. These tests are discussed in more detail in the article by J. A. Spearot in the publication of the American Chemical Society entitled "Industrial and Engineering Chemistry Product Research and Development", Vol. 13, No. 4 (1974).

The increase in oxidation and viscosity of the oil is, of course, an exponential function of time and temperature and with the advent of anti-pollutant devices, lean carburation, nonideal spark advance and increasing under-hood temperatures have caused average oil operating temperatures to rise significantly. Also, increases in average driving speed and trip duration further compound the temperature problems; see E. Gallopoulous, Society of Automotive Engineering Paper No. 7, 00506 (1970).

High temperature oil performance parameters have been established by the American Petroleum Institute and the American Society for Testing Materials. A typical premium oil, with an A.P.I. "SE" designation, is specified not to exceed 400 percent of the initial viscosity after 48 hours on an ASTM sequence IIIC engine test. The four fold increase in viscosity is considered the safe replacement point for automotive applications.

There is not available, however, a satisfactory monitoring apparatus which will monitor the engine oil to determine when the oil has degraded sufficiently by way of oxidation to increase the viscosity to the point where the oil should be changed.

The second component of the total degradation of the oil is the contamination of the oil by water, acids and sludge. Water, acid and sludge formation result primarily from piston ring and valve guide blow-by. The problem associated with water, acid and sludge formation in the oil has been reduced somewhat by corrosion inhibitors added to the lubricating oil and/or by use of effective engine oil filters. When an automotive engine is operated a relatively short period of time such as in short run driving, the lubricating oil rarely reaches a high enough predetermined temperature to boil off the water and the volatile acids which cause excessive corrosion of internal engine parts. It is possible that the total accummulated engine hours of operating time would be under operating conditions where the oil does not reach the high enough predetermined temperature to boil off the contaminants and such could severely shorten the engine life. Continuous short trip service of an automotive engine would require that the lubricating oil be changed at an interval substantially less than the norm established or suggested by the manufacturer. Short trips could be defined as those shorter than approximately three miles, which is the distance normally required to heat the lubricating oil to a temperature of approximately 210° F, which temperature would boil off the water and volatile acids or contaminants in the lubricating oil.

The subject invention provides a method and apparatus for monitoring the degradation of oil by sensing the oil temperature and the time period the oil is subjected to the temperature for producing an exponential output relating the oxidation of the oil while at the same time sensing the number of occurrences the oil is heated without reaching a predetermined temperature which would boil off contaminants for producing an additive output and summing the two outputs for producing a summation indicating the total oil degradation.

As alluded to above, the subject invention is particularly suited for monitoring the degradation of oil but also has broader applications and features such as the monitoring of the change in a material undergoing a thermally activated process which follows an exponential curve involving temperature and time with a creep material which changes in physical dimension exponentially in response to heat energy when subjected to a constant force by placing the creep material in thermal contact with the monitored material and placing the creep material under a constant force or stress.

Other advantages of the present invention will be readily appreciated as the same becomes better understood by reference to the following detailed description when considered in connection with the accompanying drawings wherein:

FIG. 1 is a side elevational view partially broken away and in cross section of an apparatus constructed in accordance with the subject invention and connected to an oil filter;

FIG. 2 is an enlarged elevational view partially in cross section of the apparatus constructed in accordance with the subject invention;

FIG. 7 is a side elevational view showing an alternative construction of one of the components of the apparatus shown in FIGS. 2 and 3;

An apparatus for monitoring the degradation of oil in accordance with the subject invention is generally shown at 10. In FIG. 1 the oil monitoring apparatus 10 is shown associated with the housing 12 of an oil filter assembly including a replaceable oil filter cartridge 14. The oil monitoring apparatus 10 is a replaceable unit which may be replaced each time the oil is changed and/or the filter cartridge 14 is changed, as will become more clear hereinafter. Thus, the oil monitoring apparatus 10 is shown as disposed within the lubricating oil as it passes through the filter housing 12. It will be appreciated, however, that the oil monitoring apparatus 10 may be placed in thermal contact with the lubricating oil in its own separate housing or even within the engine itself.

The apparatus 10 includes a first sensing means generally shown at 16 for changing in physical dimension in response to oil temperature and the time at that temperature to provide an exponential output indicating the degradation of the oil due to the oxidation of the oil. Also included is a second sensing means generally shown at 18 for producing an additive output reflecting the number of occurrences the oil is heated without reaching a high enough predetermined temperature to disperse the water, acids and sludge which contaminate the oil. Also built into the apparatus is a summing means for producing a sum of the outputs from the first and second sensing means.

Figure 6:
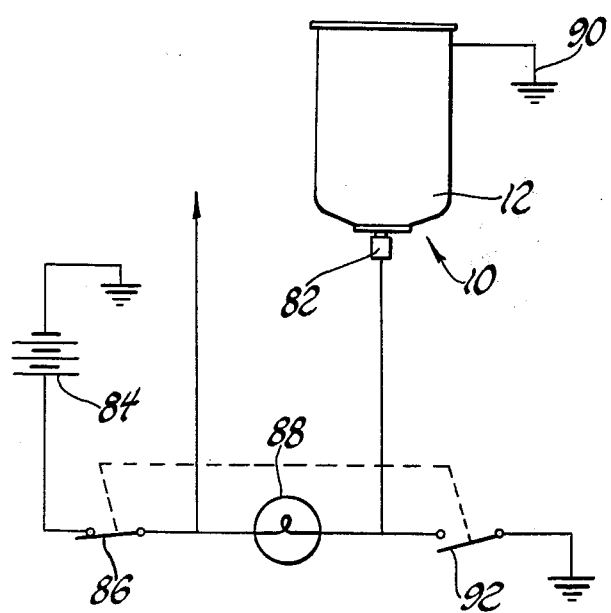
FIG. 6 shows a typical circuit for providing a signal from the apparatus shown in FIGS. 2 and 3.

The circuit represented in FIG. 6 is a part of a signal means for providing a signal when the sum of the outputs from the sensing means 16 and 18 reaches a predetermined limit.

Figure 3:
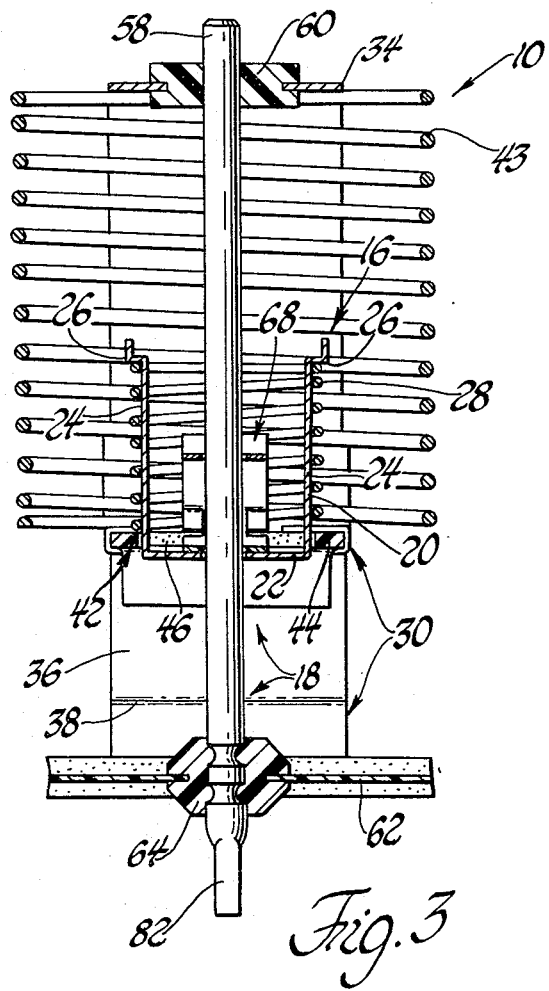
FIG. 3 is a cross-sectional view taken substantially along line 3—3 of FIG. 2.

The first sensing means 16 includes a creep means or material defined by the member 20 which changes in physical dimension in response to heat energy or temperature when under a constant force or stress. The member 20 is generally U-shaped, as best seen in FIG. 3, to include a base 22 and upwardly extending legs 24. The upward distal ends of the legs 24 include the shoulders 26 and the first sensing means 16 further includes a force means defined by the spring 28 which places the legs 24 of the creep member under a substantially constant tensile stress or force.

An alternative of these components is shown in FIG. 7 with like portions thereof indicated with like numerals but with the prime designation, all of which are described further hereinafter.

Figure 4:
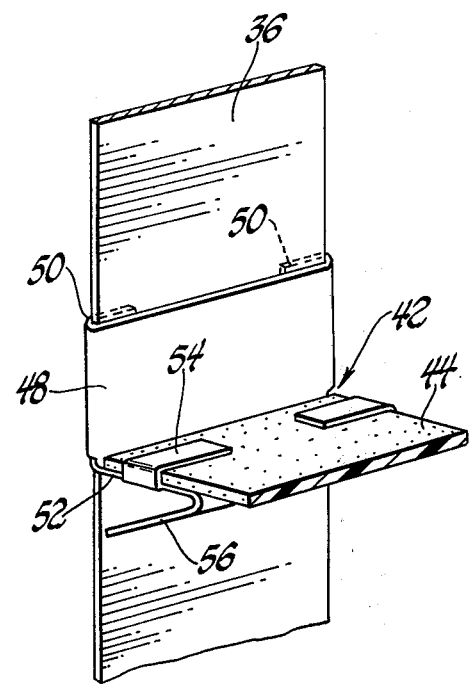
FIG. 4 is a perspective view partially in cross section showing the connection between various components of the apparatus shown in FIGS. 2 and 3.

The apparatus 10 also includes a support means generally indicated at 30 for supporting the first and second sensing means 16 and 18. The support means 30 includes a bracket means defined by the bracket member 32. The bracket member 32 is generally U-shaped with a base 34 and downwardly extending legs 36. The downward distal ends of the legs 36 have shoulders 38 and outwardly extending flanges 40. The flanges 40 define means for attaching the bracket 32 of the support means to an oil filter assembly. The support means 30 also includes platform means generally indicated at 42 for supporting the creep member 20 and the spring 28 defining the force means and is movably supported by the bracket 32. A spring 43 reacts between the base 34 of the bracket 32 and the platform means 42 merely to prevent the platform means 42 from moving upwardly due to vibrations, jolts, or the like, i.e., the spring 43 applies a very light downward load on the platform means 42. More specifically, the platform means 42 includes a plate 44 having a rectangular opening 46 therein. The plate 44 is made of an electrically insulating material which does not conduct electrical current such as a phenolic. The platform means also includes the metal guide member 48 supporting the ends of the plate 44. As best illustrated in FIG. 4, each guide member 48 has an upwardly extending portion with arms 50 embracing the legs 36 of the bracket member 32 whereby the guides 48 are slidably and movably supported by the legs 36 of the bracket 32. Each guide member 48 also includes a horizontally extending base portion 52 supporting the plate 44 with tabs 54 bent over the top of the plate 44 for securing the plate 44 to the guide members 48. Each guide member 48 also includes a stop means defined by the tangs 56 for allowing the platform means 42 to move relative to the bracket 32 only in one direction which is upwardly. The tangs 56 are defined by a rearward bend of the horizontal portions 52 and are pointed at the ends to dig into the interior surface of the legs 36. Thus, the guide members 48 may move upwardly relative to the legs 36 of the bracket 32 but are prevented from moving downwardly as the tangs 56 dig into the interior surfaces of the legs 36.

As will be appreciated, the spring 28 has one end disposed upon the plate 44 with the other end engaging the shoulder 26 of the creep member 20 to place the creep member 20 under a constant force or tensile stress.

Figure 5:
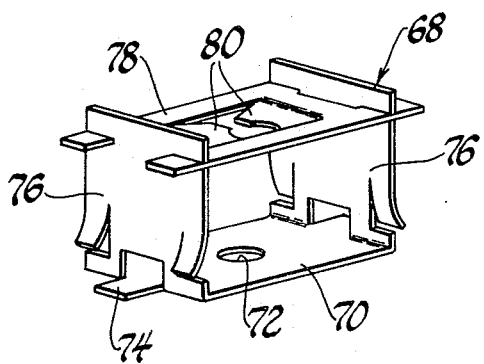
FIG. 5 is a perspective view of one of the components of the apparatus shown in FIGS. 2 and 3.

The second sensing means 18 includes a displacement means for moving the platform means 42 upwardly relative to the bracket 32 when the oil is heated without reaching a predetermined temperature. The displacement means is defined by the rod means or rod 58 which extends through the platform means 42 and through the base 34 of the bracket 32. An electrically insulating guide member 60 is supported in an aperture in the base 34 of the bracket 32 and surrounds the upper end of the rod 58. The insulating member 60 prevents the flow of electrical current between the rod 58 and the bracket 32, the purpose of which will become more clear hereinafter. The displacement means also includes the diaphragm means or diaphragm 62 which is connected to the rod 58 through an electrically insulating member 64 for moving the rod 58 in response to oil pressure. The outer periphery of the diaphragm 62 may be adhesively or otherwise secured to the flanges 40 of the bracket 32 and is circular about its periphery. The circular periphery of the diaphragm 62 is secured to and in sealing relationship to the oil filter housing 12 by the U-shaped crimp 66 in the filter housing 12. In other words, the U-shaped crimp 66 is circular in configuration and seals the diaphragm 62 in the filter housing 12. It will be appreciated, however, that the diaphragm 62 may be supported by the bracket 32 and in sealing relationship with the filter housing in various different configurations. The displacement means also includes temperature sensitive means generally indicated at 68, as best illustrated in FIG. 5. The temperature sensitive means 68 prevents movement of the platform means 42 relative to the bracket means 32 when the oil reaches a predetermined temperature. The temperature responsive means 68 interconnects the platform means 42 and the rod 58 for gripping the rod 58 below the predetermined temperature of the oil and releases the rod above that predetermined temperature whereby the rod may move without moving the platform means when the oil is above the predetermined temperature. Specifically, the temperature sensitive means 68 includes a metal frame member 70 having a hole 72 therethrough through which the rod 58 passes. The frame member 70 is disposed in the aperture 46 in the plate 44 and includes tabs 74 extending laterally to engage the bottom surface of the plate 44. The base 22 of the creep member 20 extends beneath the bottom portion of the frame member 70 whereby the creep member 20 urges the frame member 70 upwardly to maintain the tabs 74 in engagement with the plate 44 whereby the spring 28 reacts between the creep member 20 and the plate 44. The upwardly extending sides 76 of the frame 70 support a rod gripping member 78. The rod gripping member 78 is connected to the sides 76 through slots in the sides 76 and extensions of the gripping member 78. The rod gripping member 78 includes gripping tangs 80 which are normally in gripping engagement with the rod 58. However, the member 78 is preferably made of a metal or a bimetal so that the gripping tangs 80, when subjected to a predetermined temperature, deflect or bend downwardly to move out of gripping engagement with the rod 58. The gripping tangs 80 may be defined by bimetallic elements.

In operation, upon starting of an automotive engine, the oil pressure comes up to an operating condition and that pressure exists within the oil filter housing 12 and acts upon the diaphragm 62 to move the diaphragm 62 downwardly, as viewed in FIGS. 1 through 3. As the diaphragm 62 moves downwardly, it moves the rod 58 downwardly as the gripping tangs 80 allow the rod 58 to move freely downwardly. In the event the engine oil does not reach a high enough predetermined temperature to disperse the water, acid and sludge which contaminates the oil, the gripping tangs 80 remain in gripping contact with the rod 58. Thus, if the oil does not reach that predetermined temperature and the engine is shut off, the diaphragm 62 returns to the position shown and the rod 58 moves upwardly but, since the gripping tangs 80 are in gripping engagement with the rod, the entire platform means 42 is moved upwardly as the guide members 48 slide upwardly along the legs 36 of the bracket 32. Such is a cold operating condition and such cold operating position moves the platform means 42 upwardly. Of course, the gripping tangs 80 are selected from a metal which will bend or move at the predetermined temperature of the oil which is high enough to begin to disperse the contaminants. The tangs 56 allow the platform means to move upwardly but prevent the platform means 42 from moving downwardly from the position to which moved. Thus, each cold operating condition at which the engine does not reach the predetermined temperature moves the platform means 42 incrementally upwardly. The gripping tangs 80 may be made of metal and of a configuration such that they will move out of gripping engagement with the rod 58 when the oil temperature reaches 210° F, that temperature being necessary to disperse the contaminants, and so long as the oil temperature does not reach 210° F in the preferred embodiment the platform means 42 would be moved 0.0025 inches upwardly along the bracket 32 when the engine is shut off and the oil pressure goes to zero. When the oil reaches 210° F the tangs 80 move out of engagement with the rod 58 whereby the platform means 42 is not moved when the engine is shut down. During nonoperation of the engine the oil cools and the gripping tangs 80 return to gripping engagement with the rod 58.

In the event the oil temperature goes above the predetermined temperature or, as in the above example, 210° F, creep member 20 is placed under a constant force by the spring 28 and will elongate in length exponentially, the operand of the exponent being the base of the natural system of logarithms in response to the temperature of the oil and the time at that temperature. The creep member 20 is connected to and extends from the platform means 42 to the distal ends of the legs 24 thereof in the direction of movement of the platform means 42 relative to the bracket means 32 whereby the change in physical dimension of the creep member 20 is an increase in length of the legs 24 thereof between the platform means 42 of the upward distal ends of the legs 24. As the creep member 20 increases in length it remains at that increased length and as the creep member 20 increases in length the distal ends of the legs thereof are disposed closer to the base 34 or top of the bracket 32.

The signal means shown in FIG. 6 includes means for determining when the distal ends of the creep member 20 have moved to a predetermined position relative to the bracket means 32 and, specifically, when the distal ends of the creep member 20 engage the base 34 of the bracket 32 as a result of the change in length of the creep member 20 and/or movement of the platform means 42 relative to the bracket means 32. Specifically, a battery 84 supplies electrical energy through a normally closed switch 86 and a light or indicator 88 to the bottom 82 of the rod 58. There is an electrical flow path through the rod 58, the gripping tangs 80 through the frame member 72 to the metal creep member 20. The housing 12 of the filter assembly is connected to ground at 90 which, in turn, grounds the bracket 32. Thus, when the distal ends of the legs 24 of the metal creep member 20 engage the base 34 of the bracket 32 a current flow path is established lighting or energizing the indicator 88. The signal means also includes a normally open switch 92 which is mechanically connected to the switch 86 and serves as a test switch whereby upon closure of the switch 92 the switch 86 opens and a current to ground is established for testing the indicator or light 88.

Figure 9:
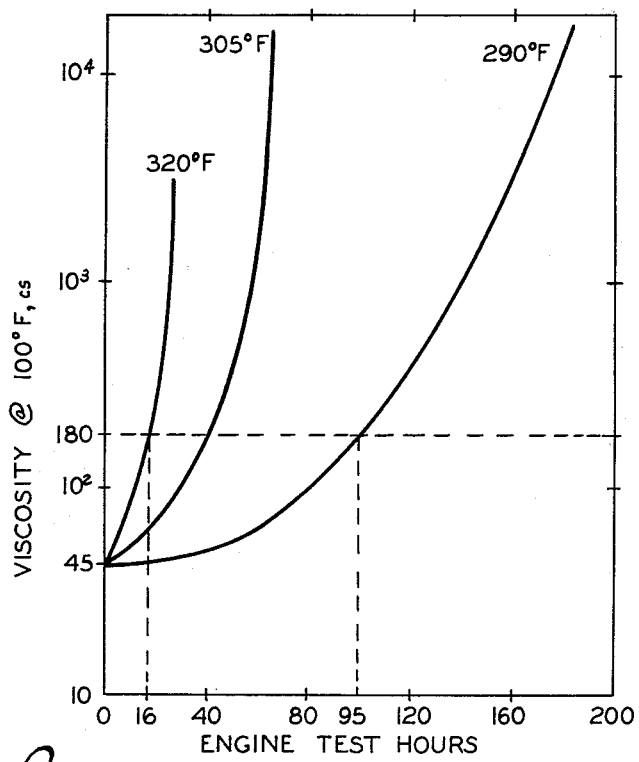
FIG. 9 is a graph showing the change in viscosity of a typical lubricating oil at particular temperatures.

FIG. 9 is a graph showing the effect of oil temperature on viscosity change and shows a typical premium grade oil with a starting viscosity of nominally 45 cs. As set forth above, it is desired that the oil be changed after a 400 percent increase in viscosity and that 400 percent increase would be 180 cs., as indicated on the graph. It will be noted that the oil reaches the 180 cs. as a function of operating temperature but at different operating temperatures the oil reaches that viscosity under different amounts of time. For example, at 320° F the oil should be changed after 16 hours whereas at an operating temperature of 290° F the oil will last 95 hours. It will be noted that the curves in FIG. 9 are exponential curves which follow the basic function expressed by the formula $t \cdot e^{-E/RT}$ where $t$ is the time in seconds where the lubricating oil is at a given temperature, $e$ is the base of natural logarithms, which is 2.7183, $E$ is the activation energy in oxidizing the particular lubricating oil measured in calories per mole, $R$ is the "gas constant" of 1.987 of the particular oil measured in calories per mole degrees Kelvin and $T$ is the temperature of the oil in degrees Kelvin. In the particular example shown in FIG. 9, the ratio of E:R in the particular lubricating oil is 18,600° K.

Figure 8:
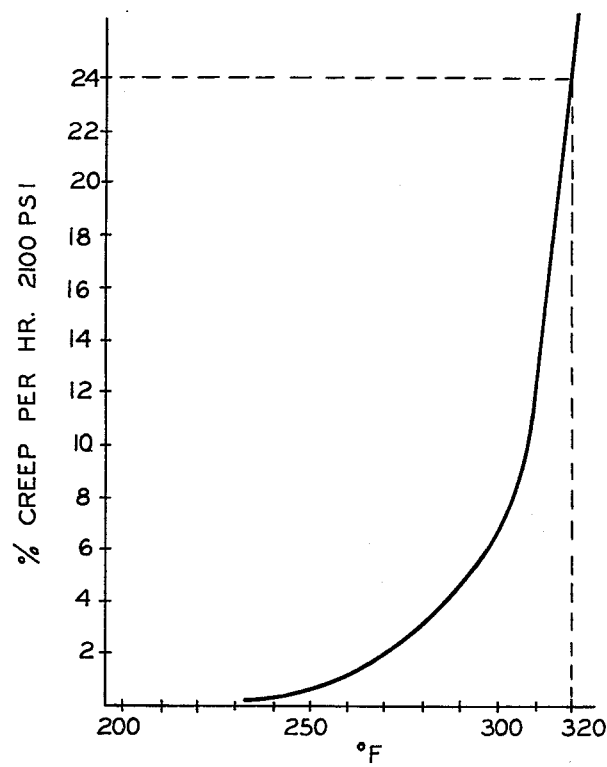
FIG. 8 is a graph showing the exponential change in physical dimension of a creep material subjected to heat and a constant force or stress.

FIG. 8 is a graph representing experimental data on the creep behaviour of super plastic NJZ 400 alloy when subjected to a constant stress of 2100 psi. The alloy is an electrochemically active material and has a 22 percent aluminum zinc alloy. The electrical chemical alloy will corrode and will be eaten away when exposed to the acids of the oil which adds another time corrosion term because the concentration of the corrosive elements in the oil will be subjected to the creep member 20 to corrode it, thereby allowing the creep member to elongate more rapidly. In other words, should the engine never be operated and the acids and corrosive elements in the oil build-up, they could corrode the creep element 20 sufficiently that it would elongate to provide the signal to change the oil.

A suitable spring 28 is selected so that an essentially constant rate of change in physical dimension or length of the creep member 20 at a given temperature is maintained. The spring force-deflection characteristic is typically parabolic. In the ideal system where the rate of change of length of the creep member 20 is a linear function of stress, the spring may be characterized by the formula $$F_n = F_o \frac{(\Delta L + L)^{-2}}{L}$$

wherein $L$ is the original length of the legs 24 of the creep member 20, $\Delta L$ is the incremental increase in the length of the creep member 20 after being subjected to the force exerted by the spring 28; $F_o$ is the original force exerted by the spring 28 on the creep member 20 and $F_n$ is the force exerted by the now extended spring 28 on the creep member 20, now of a length $L + \Delta L$.

FIG. 7 shows an alternative creep member 20'. Instead of the legs 24' thereof being straight, they include convolutions and these convolutions will be straightened in response to the exponential time temperature function under the force of the spring 28', the primary difference being that the convolutions place the legs 24' in bending under the constant stress instead of elongating or changing in length. Nevertheless, the spring 28' exerts a force which, in turn, applies a constant stress in terms of bending to the creep member 20'. The creep member 20' is also preferably made of the same alloy as the creep member 20.

The creep member 20 may have an effective length under tensile stress between the shoulders 26 and the base 22 of 0.30 inches and a permissible final length of 1.20 inches which is a 400 percent extension proportional to the 400 percent increase in the oil viscosity. A nominal starting stress of 2100 psi. is achieved by using an initial force (Fo) of 5 pounds acting on an area of $2.4 \times 10^{-3}$ in$^2$. It can be determined that at 320° F the strain rate of the creep member 20 is nominally 24 percent per hour so that in approximately 16 hours the creep member 20 will have strained to a design limit of 1.20 inches. Thus, the material of which the creep member 20 is made when placed under a constant stress and subjected to a temperature of 320° F approximates the curve of 320° F set forth in FIG. 9. In addition, at a temperature of 290° F the creep member 20 strains at a rate of 4.2 percent per hour so that approximately 95 hours are required for the element to reach the design limit of 1.20 inches and such approximates the 290° F curve of FIG. 9.

The curve of FIG. 8 is also exponential and also follows the basic equation $t \cdot e^{-E/RT}$ set forth above and which describes a thermally activated process. Therefore, it is only necessary to match the curves of the super plastic alloy, such as that shown in FIG. 8, with the curves which describe the thermally activated process taking place in the oil such as those shown in FIG. 9.

More specifically, the first sensing means 16 senses the degradation of oil due to oxidation in accordance with the integral equation $$D_1 = \int_{T\,min}^{T\,max} nt \cdot e^{-E/RT} dT$$

wherein $D_1$ is the degradation of the lubricating oil due to the oxidation of the lubricating oil; $T$ max is the highest temperature the oil reaches; $T$ min is the lowest temperature; $n$ is the oxidation constant determined by the properties of the particular lubricating oil; $t$ is the time in seconds that the lubricating oil is at a given temperature; $e$ is the base of the natural logarithms; $E$ is the activation energy in oxidizing the particular lubricating oil measured in calories per mole; $R$ is the gas constant and $T$ is temperature in degrees Kelvin.

Further, the creep member 20 changes in physical dimension or in length under a constant stress at a rate which follows the equation $$\frac{dl}{dt} = ce^{-U/RT}$$

wherein $dl/dt$ equals the change in physical dimension or length per unit of time in seconds, $c$ is a constant reflecting the physical dimensions of the creep member 20 in combination with the combination of the magnitude of the constant stress supplied by the spring 28, $e$ is the base of natural logarithms, $U$ is a constant representing the activation energy needed to cause the creep member 20 to change in length. The constant $U$ is substantially equal to the constant $E$ as set forth above so that the curve of FIG. 8 would match a selected curve of FIG. 9 at any given temperature. The curve of FIG. 9 is based on data developed by R. H. Kabel and reported in S.A.E. Transaction, Vol. 79 (3), Page 1888 (1970).

The second sensing means 18 senses the degradation of oil because of contamination in accordance with the equation $D_2 = mS$ wherein $D_2$ is the degradation of lubricating oil due to contamination by water, acid and sludge and $m$ is the corrosion constant determined by the properties of the particular lubricating oil and $S$ is the number of occurrences the oil is heated without reaching a high enough predetermined temperature to disperse the water, acids and sludge in the oil.

The apparatus 10 includes a summing means by arrangement of the components therein for producing a sum of $D_1$ and $D_2$ which is D and is the total degradation of the lubricating oil.

It would be appreciated that the first sensing means 16 may be used for monitoring a material undergoing a thermally activated process which follows an exponential curve wherein the operand of the exponent is the base of the natural system of logarithms and wherein the exponential curve involves temperature and time, as it includes a creep means for changing in physical dimension in the exponential fashion in response to heat energy when subjected to a constant force with the constant force applied to the creep means by the force means comprising the spring 28.

It will also be appreciated that the assembly 10 performs a method of monitoring the degradation of oil including the steps of sensing the oil temperature and the time period the oil is subjected to the temperature for producing an exponential output and sensing the number of occurrences oil is heated without reaching a predetermined temperature for producing an additive output and sums the two outputs for producing a summation thereof.

Further, the above formula for degradation, $D_1$ may be utilized in the sensing means 16 for monitoring the change in a material undergoing a thermally activated process which materials would include any thermosetting resin by thermally exposing the electrochemically active material, of the creep member 20 under a constant stress, to the material to be monitored.

Further, the apparatus 10 may perform the method of monitoring the change in a material undergoing a thermally activated process which follows an exponential curve involving temperature and time with a creep material which changes in thermal contact with the monitor material and placing the creep material under a constant force.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

The embodiments of the invention in which an exclusive property or privilege is claimed are defined as follows:

1. An apparatus for monitoring the degradation of oil comprising; first sensing means for producing an exponential output in response to oil temperature and the time the oil is subjected to the temperature, second sensing means for producing an additive output reflecting the number of occurrences the oil is heated without reaching a predetermined temperature, and summing means for producing a summation of said outputs.

2. An apparatus for monitoring the degradation of oil comprising; first sensing means for changing in physical dimension in response to oil temperature and the time at that temperature to provide an exponential output indicating the degradation of the oil due to the oxidation of the oil, second sensing means for producing an additive output reflecting the number of occurrences the oil is heated without reaching a high enough predetermined temperature to disperse the water, acids and sludge which contaminate the oil, and summing means for producing a sum of said outputs.

3. An apparatus as set forth in claim 2 including signal means for providing a signal when said sum of said outputs reaches a predetermined limit.

4. An assembly as set forth in claim 3 wherein said first sensing means includes creep means for changing in said physical dimension in response to heat energy when under stress, and force means for placing said creep means under stress.

5. An assembly as set forth in claim 4 wherein said force means places said creep means under a substantially constant stress.

6. An assembly as set forth in claim 5 wherein said creep means has a creep rate of change in physical dimension when under constant stress which follows the equation $$\frac{dl}{dt} = ce^{-U/RT}$$

wherein $dl$ is the change in physical dimension of said creep means, $dt$ equals the time span during which the change in physical dimension occurs, $c$ in a constant reflecting the physical dimension of said creep means in combination with the magnitude of the constant stress, $e$ is the base of natural logarithms, $U$ is a constant representing the activation energy needed to cause said creep means to change in physical dimension, $R$ is the gas constant and $T$ is the temperature of said creep means.

7. An apparatus as set forth in claim 4 including temperature sensitive means for rendering said second sensing means inactive when the oil reaches said predetermined temperature.

8. An apparatus as set forth in claim 4 including support means for supporting said sensing means, said support means including bracket means and platform means for supporting said creep means and said force means and movably supported by said bracket means.

9. An apparatus as set forth in claim 8 wherein said second sensing means includes displacement means for moving said platform means relative to said bracket means when the oil is heated without reaching said predetermined temperature.

10. An apparatus as set forth in claim 9 wherein said displacement means includes temperature sensitive means for preventing movement of said platform means relative to said bracket means when the oil reaches said predetermined temperature.

11. An apparatus as set forth in claim 10 wherein said platform means includes stop means for allowing said platform means to move relative to said bracket means only in one direction.

12. An apparatus as set forth in claim 11 wherein said displacement means includes rod means extending through said platform means, said temperature responsive means interconnecting said platform means and said rod means for gripping said rod means below said predetermined temperature and for releasing said rod above said predetermined temperature whereby said rod may move without moving said platform means above said predetermined temperature.

13. An apparatus as set forth in claim 12 wherein said creep means is connected to and extends from said platform means to a distal end in the direction of movement of said platform means relative to said bracket means, said force means disposed to react between said platform means and said distal end of said creep means whereby said change in physical dimension of said creep means in an increase in length thereof between said platform means and said distal end thereof.

14. An apparatus as set forth in claim 13 wherein said signal means includes means for determining when said distal end of said creep means has moved to a predetermined position relative to said bracket means as a result of a change in length of said creep means and/or movement of said platform means relative to said bracket means.

15. An apparatus as set forth in claim 14 wherein said creep means is made of an electrochemically active material.

16. An apparatus as set forth in claim 15 wherein said electrochemically active material is a 22 percent aluminum-zinc alloy.

17. An apparatus as set forth in claim 15 wherein said creep means has a creep rate of change in physical dimension when under constant stress which follows the equation $$\frac{dl}{dt} = ce^{-U/RT}$$

wherein $dl$ is the change in physical dimension of said creep means, $dt$ equals the time span during which the change in physical dimension occurs, $c$ is a constant reflecting the physical dimension of said creep means in combination with the magnitude of the constant stress, $e$ is the base of natural logarithms, $U$ is a constant representing the activation energy needed to cause said creep means to change in physical dimension, $R$ is the gas constant and $T$ is the temperature, of said creep means.

18. An apparatus as set forth in claim 17 wherein said displacement means includes diaphragm means connected to said rod means for moving said rod means response to oil pressure.

19. An apparatus as set forth in claim 18 wherein said support means includes means for attachment to an oil filter assembly.

20. An apparatus as set forth in claim 15 wherein said creep means includes at least one convolution along the length thereof for straightening when placed under said constant stress.

21. An apparatus for monitoring the degradation of oil comprising; first sensing means for sensing the degradation of oil in accordance with the equation $$D_1 = \int_{T_{min}}^{T_{max}} nt \cdot e^{-E/RT} dT$$

wherein $D$ is the degradation of the oil due to oxidation, $T$ max is the highest temperature of the oil, $T$ min is the lowest temperature of the oil, $n$ is the oxidation constant determined by the properties of the oil, $t$ is the time the oil is at a given temperature, $e$ is the base of natural logarithms, $E$ is the activation energy in oxidizing the oil measured in calories per mole, $R$ is the gas constant, and $T$ is the oil temperature, and support means for supporting said first sensing means.

22. An apparatus as set forth in claim 20 wherein said first sensing means includes creep means which changes in physical dimension when under constant stress at a rate which follows the equation $$\frac{dl}{dt} = ce^{-U/RT}$$

wherein $dl/dt$ equals the change in physical dimension per unit of time, $c$ is a constant reflecting the physical dimensions of said creep means in combination with the magnitude of the constant stress, $e$ is the base of material logarithms, $U$ is a constant representing the activation energy needed to cause said creep means to change in physical dimension and substantially equals the constant $E$.

23. An apparatus as set forth in claim 21 including second sensing means for sensing the degradation of oil in accordance with the equation $D_2 = mS$ wherein $D_2$ is the degradation of the oil due to contamination, $m$ is the corrosive constant determined by the properties of the oil, and $S$ is the number of occurrences the oil is heated without reaching a predetermined temperature.

24. An apparatus as set forth in claim 23 including summing means for producing a sum of $D_1$ and $D_2$.

25. An apparatus as set forth in claim 24 including signal means for producing a signal when said sum reaches a predetermined limit.

26. An apparatus for monitoring a material undergoing a thermally activated process defined by the function $t \cdot e^{-K/T}$ wherein $t$ is time in seconds, $e$ is the base of natural logarithms, $K$ is a constant including the activation energy of the process measured in calories per mole; said apparatus comprising; support means, creep means supported by said support means and having a rate of change in physical dimension which follows the equation $$\frac{dl}{dt} = ce^{-U/RT}$$

when subjected to a constant force wherein $dl/dt$ equals the rate of change in physical dimension, $c$ is a constant determined by the physical dimensions of said creep means and the magnitude of the constant force, $e$ is the base of natural logarithms, $U$ is the activation energy required for said creep means to change in physical dimension, $R$ is the gas constant, $T$ is temperature, and wherein $U/R$ is substantially equal to $K$.

27. An apparatus as set forth in claim 26 wherein said creep means includes an electrochemically activated material.

28. An apparatus as set forth in claim 27 wherein said electrochemically activated material comprises a 22 percent aluminum-zinc alloy.

29. An apparatus for monitoring a material undergoing a thermally activated process which follows an exponential curve involving temperature and time comprising, creep means for changing in physical dimension exponentially in response to heat energy when subjected to a constant stress, and force means for placing said creep means under a constant stress.

30. An apparatus as set forth in claim 29 including signal means for providing a signal in response to the change in physical dimension of said creep means.

31. An apparatus for monitoring the degradation of oil comprising; sensing means for mechanically producing an additive output movement reflecting the number of occurrences the oil is heated without reaching a predetermined temperature, and signal means for producing a signal when said output movement reaches a predetermined amount.

32. An apparatus as set forth in claim 31 including temperature sensitive means for rendering said sensing means inactive when the oil reaches said predetermined temperature.

33. An apparatus as set forth in claim 31 wherein said sensing means includes bracket means, platform means movably supported by said bracket means, and displacement means for moving said platform means relative to said bracket means.

34. An apparatus as set forth in claim 33 including temperature sensitive means for preventing movement of said platform means relative to said bracket means when the oil reaches said predetermined temperature.

35. An apparatus as set forth in claim 34 wherein said platform means includes stop means for allowing said platform means to move relative to said bracket means only in one direction.

36. A method of monitoring the degradation of oil comprising the steps of; sensing oil temperature and the time period the oil is subjected to the temperature for producing an exponential output, sensing the number of occurrences the oil is heated without reaching a predetermined temperature for producing an additive output, and summing said outputs for producing a summation thereof.

37. A method as set forth in claim 36 including the step of providing a signal when said summation of said outputs reaches a predetermined limit.

38. A method of monitoring the degradation of oil comprising the steps of; sensing the oxidation of the oil with a material which changes physically to produce an exponential output in response to oil temperature and the time at that temperature, sensing the number of occurrences the oil is heated without reaching the high enough predetermined temperature to disperse the water, acids and sludge therein which contaminate the oil for producing an additive output reflecting the number, and summing the outputs for producing a summation thereof.

39. A method as set forth in claim 38 including the step of providing a signal when said summation of said outputs reaches a predetermined limit.

40. A method of monitoring the degradation of oil due to oxidation in accordance with the formula $$D_1 = \int_{T\,min}^{T\,max} nt \cdot e^{-E/RT} dT$$

wherein $D_1$ is the degradation of the oil due to oxidation, $T$ max is the highest temperature of the oil, $T$ min is the lowest temperature of the oil, $n$ is the oxidation constant determined by the properties of the oil, $t$ is the time the oil is at a given temperature, $e$ is the base of natural logarithms, $E$ is the activation energy in oxidizing the oil measured in calories per mole, $R$ is the gas constant, and $T$ is the oil temperature, said method including the steps of exposing the oil to an electrochemically active material which creeps when under constant stress at a rate which follows the equation $$\frac{dl}{dt} = ce^{-U/RT}$$

wherein $dl/dt$ equals the change in physical dimension per unit of time, $c$ is a constant reflecting the physical dimensions of said material in combination with the magnitude of the constant stress, $e$ is the base of natural logarithms, $U$ is a constant representing the activation energy needed to cause the material to change in physical dimension and substantially equals $E$; and sensing a predetermined change in the physical dimension of the material.

41. A method as set forth in claim 40 including sensing the degradation of the oil in accordance with the equation $D_2 = mS$ wherein $D_2$ is the degradation of the oil due to contamination, $m$ is the corrosive constant determined by the properties of the oil, and $S$ is the number of occurrences the oil is heated without reaching a predetermined temperature.

42. A method as set forth in claim 41 including the step of summing $D_1$ and $D_2$.

43. A method as set forth in claim 42 including the step of providing a signal when the summation of $D_1$ and $D_2$ reaches a predetermined limit.

44. A method of monitoring the change in thermosetting resin material undergoing a thermally activated process in accordance with the formula $$D_1 = \int_{T\,min}^{T\,max} nt \cdot e^{-E/RT} dT$$

wherein $D_1$ is the change in the material, $T$ max is the highest temperature of the material, $T$ min is the lowest temperature of the material, $n$ is a constant determined by the properties of the material, $t$ is the time the material is at a given temperature, $e$ is the base of natural logarithms, $E$ is the activation energy in changing the material measured in calories per mole, $R$ is the gas constant, and $T$ is the material temperature, said method including the steps of exposing the material to an electrochemically active creep material which creeps when under constant stress at a rate which follows the equation $$\frac{dl}{dt} = ce^{-U/RT}$$

wherein $dl/dt$ equals the change in physical dimension per unit of time, $c$ is a constant reflecting the physical dimensions of said creep material in combination with the magnitude of the constant stress, $e$ is the base of natural logarithms, $U$ is a constant representing the activation energy needed to cause the creep material to change in physical dimension and substantially equals $E$; and sensing a predetermined change in the physical dimension of the creep material.

45. A method of monitoring the change in a material undergoing a thermally activated process which follows an exponential curve involving temperature and time with a creep material which changes in physical dimension exponentially in response to heat energy when subjected to a constant force, said method comprising the steps of; placing the creep material in thermal contact with the monitored material, and placing the creep material under a constant force.

46. A method as set forth in claim 45 including the step of sensing the change in physical dimension of the creep material.

47. A method of monitoring the degradation of oil comprising the steps of; mechanically sensing the number of occurrences the oil is heated without reaching a predetermined temperature for providing an additive output movement, and producing a signal when said output movement reaches a predetermined amount.

48. A method of monitoring the degradation of oil comprising the steps of; moving a first member relative to a second member in a first direction each time the oil is heated, moving the first member in the opposite direction when the oil is no longer being heated, moving the second member in the opposite direction with the first member when the oil fails to reach a predetermined temperature and failing to move the second member with the first member when the oil exceeds the predetermined temperature.

49. A method as set forth in claim 48 including providing a signal when the second member has been moved a predetermined distance.

* * * * *